United States Patent [19]
Plochocka

[11] Patent Number: 5,939,506
[45] Date of Patent: Aug. 17, 1999

[54] SOLVENT-FREE PROCESS FOR MAKING HIGH MOLECULAR WEIGHT TERPOLYMERS OF MALEIC ANHYDRIDE, $C_1$-$C_4$ ALKYL VINYL ETHER AND ISOBUTYLENE

[75] Inventor: Krystyna Plochocka, Scotch Plains, N.J.

[73] Assignee: ISP Investments Inc., Wilmington, Del.

[21] Appl. No.: 08/942,830

[22] Filed: Oct. 2, 1997

[51] Int. Cl.⁶ .................................................. C08F 222/04
[52] U.S. Cl. ............................................................ 526/272
[58] Field of Search ............................................... 526/272

[56] References Cited

U.S. PATENT DOCUMENTS

| | | | |
|---|---|---|---|
| 4,358,573 | 11/1982 | Verbrugge | 526/272 |
| 4,780,499 | 10/1988 | Villarreal et al. | 526/272 |
| 5,037,924 | 8/1991 | Tazi et al. | 526/272 |
| 5,082,913 | 1/1992 | Tazi et al. | 526/272 |
| 5,221,787 | 6/1993 | Robison et al. | 526/272 |
| 5,237,027 | 8/1993 | Kawame et al. | 526/272 |
| 5,340,918 | 8/1994 | Kittrell et al. | 526/272 |

FOREIGN PATENT DOCUMENTS

| | | | |
|---|---|---|---|
| 44-20993 | 9/1969 | Japan | 526/272 |
| 0381386 | 4/1991 | Japan | 526/272 |
| 3109404 | 5/1991 | Japan | 526/272 |
| 0562092 | 6/1944 | United Kingdom | 526/272 |
| 1028231 | 5/1966 | United Kingdom | 526/272 |
| 1087075 | 10/1967 | United Kingdom | 526/272 |

*Primary Examiner*—Bernard Lipman
*Assistant Examiner*—N. Sarofim
*Attorney, Agent, or Firm*—Walter Katz; William J. Davis; Marilyn J. Maue

[57] ABSTRACT

This invention relates to high molecular weight terpolymers of maleic anhydride, $C_1$–$C_4$ alkyl vinyl ethers and isobutylene, and to a solvent-free process for making such terpolymers, which are particularly useful as starting materials for denture adhesives.

9 Claims, No Drawings

SOLVENT-FREE PROCESS FOR MAKING HIGH MOLECULAR WEIGHT TERPOLYMERS OF MALEIC ANHYDRIDE, $C_1$-$C_4$ ALKYL VINYL ETHER AND ISOBUTYLENE

BACKGROUND OF THE INVENTION

1. Field of the Invention

This invention relates to high molecular weight terpolymers of maleic anhydride (MAN), $C_1$-$C_4$ alkyl vinyl ethers (AVE), and isobutylene (IB), and, more particularly, to a solvent-free process for making such terpolymers.

2. Detailed Description of the Prior Art

U.S. Pat. No. 5,037,924 described the preparation of terpolymers of maleic anhydride, a $C_1$-$C_4$ alkyl vinyl ether, and isobutylene, for use as denture adhesives in the form of their mixed salts. These terpolymers were made by precipitation polymerization in the presence of an added solvent, for example, a cosolvent system of ethyl acetate and cyclohexane. The resultant terpolymer had a low molecular weight of about 30,000 to 400,000, with relatively good performance, in the form of their mixed salts, as denture adhesives. Furthermore, the terpolymers and their salts made therein in U.S. Pat. No. 5,037,924 contain trace amounts of the ethyl acetate and cyclohexane solvents.

Accordingly, it is an object of this invention to provide a solvent-free process of making high molecular weight terpolymers of MAN, an AVE and IB.

A specific object herein is to provide such terpolymers with molecular weights of at least about 1,500,000, which, in the form of their mixed salts, perform in an excellent manner as denture adhesives.

These and other objects and features of the invention will be made apparent from the following more particular description of the invention.

SUMMARY OF THE INVENTION

What is described herein is a solvent-free process for making fine powders of high molecular weight alternating terpolymers of maleic anhydride (MAN), a $C_1$-$C_4$ alkyl vinyl ether (AVE) and isobutylene (IB), having molecular structure of $(A-B)_n$, where A=MAN and B=AVE or IB and containing preferably about 5 to 25 mole % of isobutylene.

The NMR spectra of these terpolymers show an alternating molecular structure $(A-B)_n$ as described above, where n is such that the terpolymer has a weight average molecular weight (GPC, water pH 9) in excess of about 1,500,000, and a specific viscosity which is $\geq 6$ (1% in DMF, 25° C.).

The solvent-free process of the invention is carried out by charging the alkyl vinyl ether and isobutylene into a reactor at a mole ratio of isobutylene to alkyl vinyl ether which is substantially greater than that desired in the terpolymer, adding a radical initiator, heating the mixture to a reaction temperature of about 50 to 100° C., and feeding molten maleic anhydride over time into the reactor, wherein the mole ratio of maleic anhydride to the total charge of alkyl vinyl ether and isobutylene is not higher than 1:3. The resulting terpolymers obtained herein are odorless and free of the trace amounts of solvents characteristic of other known processes for making such terpolymers.

DETAILED DESCRIPTION OF THE INVENTION

In accordance with the invention, there is provided a solvent-free process for making high molecular weight terpolymers of maleic anhydride, a $C_1$-$C_4$ alkyl vinyl ether, preferably methyl vinyl ether, and isobutylene, having alternating molecular structure $(A-B)_n$, where A=MAN and B=AVE or IB. The terpolymers have a molar ratio of maleic anhydride to alkyl vinyl ether to isobutylene of about 0.50:0.45–0.25:0.05–0.25, respectively. Preferably the terpolymer includes about 5–25 mole % of IB. A most preferred composition has 10–15% IB, as defined above. The molecular weight is at least 1,500,000 (GPC, water, pH 9), and the specific viscosity (SV) is $\geq 6$ (1% in DMF, 25° C.).

The mixed salt of the terpolymer, e.g. a Ca/Na or Ca/Zn mixed salt, exhibits excellent performance properties when used as a denture adhesive.

The terpolymers are obtained as solvent-free, fine white powders.

A feature of the process of the invention is solvent-free polymerization process which is carried out using an excess of alkyl vinyl ether and isobutylene as the reaction medium. Accordingly, the polymerization reaction is carried out by precharging an AVE/IB mixture of predetermined composition into the reactor, adding a radical initiator, heating to a reaction temperature of about 50° to 100° C., and feeding molten maleic anhydride into the reactor over time.

The mole ratio of MAN to the total of MVE+IB is not higher than 1:3, preferably less than 1:5. Furthermore, the mole ratio of IB to MVE in precharge is made significantly higher than that desired in the terpolymer, preferably about 1:1 IB:MVE for a terpolymer containing 1:2 IB:MVE and about 1:2 IB:MVE for a terpolymer containing 1:4 IB:MVE.

Generally, an additional amount of MVE is added near the end of the polymerization in order to complete use of MAN reactant.

After stripping the remaining MVE and IB, the product is obtained as a fine odorless powder, without a solvent.

The invention will now be described with reference to the following examples.

EXAMPLE 1

A 1-liter Parr stainless steel reactor equipped with an agitator, heating mantle and syringe pumps for charging reagents was sparged with nitrogen and charged with 175 g (3.00 mole) of methyl vinyl ether (MVE), 175 g (3.12 mole) of isobutylene (IB) and 0.10 g of lauroyl peroxide. The mole ratio of MVE to IB was 0.96. The charged reactor was heated to 63° C. and the temperature was maintained while molten maleic anhydride (MAN) in an amount of 39.2 g (0.400 mole) was fed into the reactor over a period of 2 hours. The mole ratio of MVE and IB to MAN was 15.3. After holding for 3 hours at 65° C., an additional amount of 50 g (0.86 mole) MVE was added. Then the temperature was raised to 70° C. and maintained for 1 hour. Thereafter the reactor was cooled to room temperature, the pressure was released and the reactor discharged. The reaction product was recovered as a fine, white powder which was dried for 1 hour in a vacuum oven at 65° C. The product was a uniform, fine white powder (62 g), without any unreacted MAN. The specific viscosity (SV), as measured in a 1% DMF solution at 25° C. was 6.94. A $^{13}C$ NMR spectrum showed that the mole ratio of monomers in the terpolymer of MAN:MVE:IB was 0.50:0.34:0.16. The weight average molecular weight (GPC, water, pH 9) of the powder was 2,170,000.

EXAMPLE 2–5

The procedure of Example 1 was followed to provide terpolymers having different ratios of MAN:MVE:IB. The results are shown in Table 1 below.

TABLE 1

| Polymer | Example No. | | | |
|---|---|---|---|---|
| | 2 | 3 | 4 | 5 |
| MVE, g (mol) | 100 (1.72) | 200 (344) | 167 (2.87) | 200 (3.44) |
| IB, g (mol) | 150 (2.67) | 50 (0.89) | 83 (1.49) | 25 (0.44) |
| MAN, g (mol) | 41 (0.418) | 41 (0.418) | 41 (0.418) | 41 (0.418) |
| MVE/IB ratio in the reaction (by mole) | 0.39:0.61 | 0.79:0.11 | 0.66:0.34 | 0.89:0.11 |
| MAN:MVE:IB ratio in polymer (by $^{13}$C NMR, in mole fractions) | 0.50:0.28:0.21 | 0.50:0.46:0.07 | 0.50:0.40:0.10 | 0.50:0.44:0.05 |
| SV (1%, DMF) | 7.71 | 11.11 | 6.96 | 14.46 |
| Mw (GPC, water, pH 9) | 2,100,000 | 2,101,000 | 2,180,000 | 2,150,000 |

EXAMPLE 6

The terpolymers of Examples 1–5 were converted to their Ca/Na (7/2 by equiv.) and Ca/Zn (3/1 by equiv.) polysalts, at 70% neutralization of carboxyl groups. The salts were compared to equivalent reference salts made from Gantrez® AN 169 BF, i.e. to a commercially available MAN-MVE (1:1) copolymer, commonly used as a starting material for denture adhesives.

The reference Gantrez® AN 169 BF material was selected to have a molecular weight of 2,450,000 (GPC) which was higher than any of the invention terpolymers in Examples 1 through 5 herein. Therefore, any advantage in performance, of the invention terpolymers can be attributed to their molecular structure, rather than to their particular molecular weight. The terpolymer salts of the invention containing 5 to 25% IB, preferably 10–15% IB, exhibited significantly longer and stronger hold than the reference material based on results of standard denture adhesive testing, according to the procedure described in detail in U.S. Pat. No. 5,037,924.

In contrast, a MAN-MVE-IB copolymer with monomer ratios of 0.50:0.37:0.13 and a molecular weight of 223,000, made according to U.S. Pat. No. 5,037,924, displayed significantly poorer performance in denture adhesives than a Gantrez® AN 169 BF reference material. Similarly, high molecular weight MAN-MVE-IB terpolymers having less than about 5% or more than about 25% IB did not show any significant improvement in performance as a denture adhesive as compared to the Gantrez® AN 169 reference.

While the invention has been described with particular reference to certain embodiments thereof, it will be understood that changes and modifications may be made which are within the skill of the art. Accordingly, it is intended to be bound only by the following claims, in which:

What is claimed is:

1. A solvent-free process for making solvent-free, fine powders of high molecular weight alternating terpolymers of maleic anhydride, a $C_1$–$C_4$ alkyl vinyl ether and isobutylene having molecular structure $(A-B)_n$, where A is maleic anhydride and B is alkyl vinyl ether or isobutylene and containing about 5 to 25 molar % of isobutylene, which have a weight average molecular weight (GPC, water, pH 9) in excess of about 1,500,000, and a specific viscosity $\geq 6$ (1% in DMF), which comprises charging the alkyl vinyl ether and isobutylene into a reactor, the mole ratio of isobutylene to alkyl vinyl ether being substantially greater than that desired in the terpolymer, adding a radical initiator, heating the mixture to a reaction temperature of about 50 to 100° C., feeding molten maleic anhydride into the thus charged reactor over time, the mole ratio of maleic anhydride fed therein to the total charge of alkyl vinyl ether and isobutylene being no higher than 1:3.

2. A process according to claim 1 wherein said $C_1$–$C_4$ alkyl vinyl ether is methyl vinyl ether.

3. A process according to claim 1 wherein the mole ratio of maleic anhydride to alkyl vinyl ether to isobutylene in the terpolymer is 0.50:0.45–0.25:0.05–0.25, respectively.

4. A process according to claim 1 in which the terpolymer includes about 10 to 15 mole % isobutylene.

5. A process according to claim 1 wherein the mole ratio of isobutylene to alkyl vinyl ether in the charge is about 1:1 for a terpolymer with about 1:2 ratio of said monomers.

6. A process according to claim 1 wherein the mole ratio of isobutylene to alkyl vinyl ether in the precharge is about 1:2 for a terpolymer with about 1:4 ratio of said monomers.

7. A process which is carried out by precharging the isobutylene and alkyl vinyl ether monomers into a reactor and feeding molten maleic anhydride therein over time.

8. A process according to claim 7 wherein an additional amount of alkyl vinyl ether is added to complete the reaction.

9. A process according to claim 8 wherein excess isobutylene and alkyl vinyl ether is stripped after the polymerization is complete.

* * * * *